United States Patent [19]
Bandman et al.

[11] Patent Number: 5,981,192
[45] Date of Patent: Nov. 9, 1999

[54] METHOD OF DETECTING A NUCLEIC ACID ENCODING A VESICLE TRANSPORT PROTEIN

[75] Inventors: Olga Bandman; Neil C. Corley, both of Mountain View; Preeti Lal, Santa Clara, all of Calif.

[73] Assignee: Incyte Pharmaceuticals, Inc., Palo Alto, Calif.

[21] Appl. No.: 09/191,279

[22] Filed: Nov. 12, 1998

Related U.S. Application Data

[62] Division of application No. 08/900,927, Jul. 25, 1997, Pat. No. 5,840,537.

[51] Int. Cl.$^6$ .............................. C12Q 1/68; C07H 21/04
[52] U.S. Cl. ........................... 435/6; 536/23.1; 536/24.31
[58] Field of Search ................................ 435/6; 536/23.1, 536/24.31

[56] References Cited

PUBLICATIONS

Rothman, J.E., et al., "Protein Sorting by Transport Vesicles", *Science*, 272:227–234 (1996). (GI 642025) (GI 642026).

Tellam, J.T., et al., "Molecular Identification of Two Novel Munc–18 Isoforms Expressed in Non–neuronal Tissues", *Journal of Biological Chemistry*, 270: 5857–5863 (1995).

Hata, Y., et al., "A Novel Ubiquitous Form of Munc–18 Interacts with Multiple Syntaxins", *Journal of Biological Chemistry*, 270:13022–13028 (1995).

Katagiri, H., et al., "A Novel Isoform of Syntaxin–binding Protein Homologous to Yeast Sec1 Expressed Ubiquitously in Mammalian Cells", *Journal of Biological Chemistry*, 270:4963–4966 (1995).

Fujita, Y., et al., "Phosphorylation of Munc–18/n–Sec1/rbSec1 by Protein Kinase C", *Journal Biological Chemistry*, 271:7265–7268 (1996).

Tellam, J.T., et al., (GI 642025) GenBank Sequence Database (Accession U19520), National Center for Biotechnology Information: National Library of Medicine, Bethesda, Maryland 20849. (GI 642026).

Riento, K., et al., (GI 1246216) GenBank Sequence Database (Accession L41609), National Center for Biotechnology Information: National Library of Medicine, Bethesda, Maryland 20849. (GI 1246217).

Veerasamy, R., et al., "Identification of a Novel Syntaxin– and Synaptobrevin/VAMP–binding Protein, SNAP–23, Expressed in Non–neuronal Tissues", *Journal of Biological Chemistry*, 271:13300–13303 (1996).

Ziegler, S.F., et al. (GI 1480868) GenBank Sequence Database (Accession U63533), National Center for Biotechnology Information: National Library of Medicine, Bethesda, Maryland 20849. (1996).

Abe, Y. GenBank. Accession #AB002559. (1997).

*Primary Examiner*—George C. Elliott
*Assistant Examiner*—Andrew Wang
*Attorney, Agent, or Firm*—Incyte Pharmaceuticals, Inc.

[57] ABSTRACT

The invention provides a human vesicle transport protein (NVTP-1) and polynucleotides which identify and encode NVTP-1. The invention also provides expression vectors, host cells, agonists, antibodies and antagonists. The invention also provides methods for treating disorders associated with expression of NVTP-1.

2 Claims, 13 Drawing Sheets

```
                                                                                        54
5' NGG CGG CGC CCC TCG GGG AAG ATG GCG CCC TCG GGG AAG CTG AAG GCG GTG GTG GGG
                                    M   A   P   S   G   L   K   A   V   V   G 63                                                                                108
GAA AAA ATT CTG AGC GGA GTT ATT CGG AGT GTC AAG AAG GAT GGG GAG TGG AAG
 E   K   I   L   S   G   V   I   R   S   V   K   K   D   G   E   W   K 117                                                                               162
GTG CTT ATC ATG GAT CAC CCA AGC CAC ATG CGC ATC TTG TCT TCC TGC TGC AAA ATG
 V   L   I   M   D   H   P   S   H   M   R   I   L   S   S   C   C   K   M 171                                                                               216
TCA GAT ATC CTG GCT GAG GGC ATT ACC ATT GTT GAA GAC ATC AAC AAA CGG CGG
 S   D   I   L   A   E   G   I   T   I   V   E   D   I   N   K   R   R 225                                                                               270
GAA CCC ATT CCC AGT GAG GCC CTG GAG GCC ATT TAT TTG CTG AGC CCC ACG GAG AAG TCG
 E   P   I   P   S   E   A   L   E   A   I   Y   L   L   S   P   T   E   K   S 279                                                                               324
GTT CAG GCC ATC AAA GAC TTC CAG GGG ACC CCG ACT TTC ACC TAC AAA GCG
 V   Q   A   I   K   D   F   Q   G   T   P   T   F   T   Y   K   A 333                                                                               378
GCC CAT ATC TTC TTC GAC ACC TGC CCC GAG CCC CTG TTC AGT GAG CTA GGC
 A   H   I   F   F   D   T   C   P   E   P   L   F   S   E   L   G

FIGURE 1A
```

```
      387            396            405            414            423            432
CGC TCT CGT CTG GCA AAG GTG GTG AAG ACG TTG AAG GAG ATT CAC CTT GCC TTC
 R   S   R   L   A   K   V   V   K   T   L   K   E   I   H   L   A   F 441            450            459            468            477            486
CTC CCC TAC GAG GCC CAG GTG TCC TTC CTC GAT GCT CCC CAC AGC ACC TAC AAC
 L   P   Y   E   A   Q   V   S   F   L   D   A   P   H   S   T   Y   N 495            504            513            522            531            540
CTC TAC TGC CCC TTC CGG GCA GAG GAG CGC ACG CAG CTC GAG GTG CTG GCC
 L   Y   C   P   F   R   A   E   E   R   T   Q   L   E   V   L   A 549            558            567            576            585            594
CAG CAG ATT GCC ACG CTG TGC GCC ACC CTG CAG GAG TAC CCG GCC ATC CGC TAC
 Q   Q   I   A   T   L   C   A   T   L   Q   E   Y   P   A   I   R   Y 603            612            621            630            639            648
CGC AAG GGC CCA GAG GAC ACA GCC ACT CCC AGT CTG GGC CAC GCC GTC CTG GCC AAG CTG
 R   K   G   P   E   D   T   A   T   P   S   L   G   E   H   A   V   L   A   K   L 657            666            675            684            693            702
AAC GCC TTC AAG GCA GAC ACT CCC AGT CTG GGC GAG GGC CCA GAG AAA ACC CGC
 N   A   F   K   A   D   T   P   S   L   G   E   G   P   E   K   T   R 711            720            729            738            747            756
TCC CAG CTG CTG ATA ATG GAC CGG GCA GCT GAC CCC GTG TCC CCA CTA CTG CAT
 S   Q   L   L   I   M   D   R   A   A   D   P   V   S   P   L   L   H
```

FIGURE 1B

```
      765            774            783            792            801            810
GAG CTC ACG TTC CAG GCC ATG GCG TAT GAT CTG CTG GAC ATA GAG CAG GAC ACA
 E   L   T   F   Q   A   M   A   Y   D   L   L   D   I   E   Q   D   T 819            828            837            846            855            864
TAC AGG TAT GAG ACC ACC GGG CTG AGC GAG GCG CGG GAG AAG GCC GTC TTG CTG
 Y   R   Y   E   T   T   G   L   S   E   A   R   E   K   A   V   L   L 873            882            891            900            909            918
GAC GAG GAT GAC TTG TGG GTG GAG CTT CGC CAC ATG CAT ATC GCA GAT GTG
 D   E   D   D   L   W   V   E   L   R   H   M   H   I   A   D   V 927            936            945            954            963            972
TCC AAG AAG GTC ACG GAG CTC CTG AGG ACC TTC TGT GAG AGC AAG GGG CTG ACC
 S   K   K   V   T   E   L   L   R   T   F   C   E   S   K   G   L   T 981            990            999            1008           1017           1026
ACG GAC AAG GCG AAC ATC AAA GAC CTA TCC CAG ATC CTG AAA AAG ATG CCG CAG
 T   D   K   A   N   I   K   D   L   S   Q   I   L   K   K   M   P   Q 1035           1044           1053           1062           1071           1080
TAC CAG AAG GAG CTG AAT AAG TAT TCT ACG CAC CTG CAT CTA GCA GAT GAT TGT
 Y   Q   K   E   L   N   K   Y   S   T   H   L   H   L   A   D   D   C 1089           1098           1107           1116           1125           1134
ATG AAG CAC TTC AAG GGC TCG GTG GAG AAG CTG TGT AGT GTG GAG CAG GAC CTG
 M   K   H   F   K   G   S   V   E   K   L   C   S   V   E   Q   D   L
```

FIGURE 1C

```
      1143              1152              1161              1170              1179              1188
GCC ATG GGC TCC GAC GCA GAG GGG GAG AAG ATC AAG GAC TCC ATG AAG CTG ATC
 A   M   G   S   D   A   E   G   E   K   I   K   D   S   M   K   L   I 1197              1206              1215              1224              1233              1242
GTT CCG GTG CTG CTG GAC GCG GCG GTG CCC GCC TAC GAC AAG ATC CGG GTC CTG
 V   P   V   L   L   D   A   A   V   P   A   Y   D   K   I   R   V   L 1251              1260              1269              1278              1287              1296
CTG CTC TAC ATC CTC CTT CGG AAT GGT GTG AGT GAG GAG AAC CTG GCC AAG CTG
 L   L   Y   I   L   L   R   N   G   V   S   E   E   N   L   A   K   L 1305              1314              1323              1332              1341              1350
ATC CAG CAT GCC AAT GTA CAG GCG CAC AGC AGC CTC ATC CGT AAC CTG GAG CAG
 I   Q   H   A   N   V   Q   A   H   S   S   L   I   R   N   L   E   Q 1359              1368              1377              1386              1395              1404
CTG GGA GGC ACT GTC ACC AAC CCC GGG GGC TCG AGC ACC TCC AGC CGG CTG GAG
 L   G   G   T   V   T   N   P   G   G   S   S   T   S   S   R   L   E 1413              1422              1431              1440              1449              1458
CCG AGA GAA CGC ATG GAG CCC ACC TAT CAG CTG TCC CGC TGG ACC CCG GTC ATC
 P   R   E   R   M   E   P   T   Y   Q   L   S   R   W   T   P   V   I 1467              1476              1485              1494              1503              1512
AAG GAT GTA ATG GAG GAC GCC GTG GAG GAC CGG CTG GAC AGG AAC CTG TGG CCC
 K   D   V   M   E   D   A   V   E   D   R   L   D   R   N   L   W   P
```

FIGURE 1D

```
        1521            1530           1539           1548           1557          1566
TTC GTA TCC GAC CCC GCC CCC ACG GCC AGC TCC CAG GCC GCT GTC AGT GCC CGC
 F   V   S   D   P   A   P   T   A   S   S   Q   A   A   V   S   A   R 1575            1584           1593           1602           1611          1620
TTC GGT CAC TGG CAC AAG AAC AAG AAG GCT GGC GTA GAA GCC CGG GCG GGC CCC CGG
 F   G   H   W   H   K   N   K   K   A   G   V   E   A   R   A   G   P   R 1629            1638           1647           1656           1665          1674
CTC ATC GTG TAT GTC ATG GGC GGT GTG GCC ATG TCA GAG ATG AGG GCC GCC TAC
 L   I   V   Y   V   M   G   G   V   A   M   S   E   M   R   A   A   Y 1683            1692           1701           1710           1719          1728
GAG GTG ACC AGG GCC ACC GAG GGC AAG TGG GAG GTG CTC ATT GGC TCC TCA CAC
 E   V   T   R   A   T   E   G   K   W   E   V   L   I   G   S   S   H 1737            1746           1755           1764           1773          1782
ATC CTC ACC CCG ACC CGC TTC CTG GAT GAC CTG AAG GCA CTG GAC AAG AAG CTG
 I   L   T   P   T   R   F   L   D   D   L   K   A   L   D   K   K   L 1791            1800           1809           1818           1827          1836
GAG GAC ATT GCC CTG CCC TGA CCC CTG GCC CCG CCC CCT ACC CCT CCC TTT CCA
 E   D   I   A   L   P 1845            1854           1863           1872           1881          1890
GAG AAA ACT TAA ACT CTT CCC GTC GCT CTG CCA AGA TTA TCA TGT CTC AGC CTC CTG

FIGURE 1E
```

```
     1899        1908        1917        1926        1935        1944
CTA CCC ATT ACA GGT GAG AAA TGT ATC TCT TAA TCT ACG AGA TCT CAT TGG CCT 1953        1962        1971        1980        1989        1998
TAC GTT TCA GCC ATA CGT TTA TTA CCT GTA TGA TGC CCT TTC CTA TAT CGT GCC 2007        2016        2025        2034        2043        2052
TCT ACC TGT TCG GAT CCT ATT CTA TGG CCT CCT GGG AAG GTT TAC GAT GGT CAC 2061        2070        2079        2088        2097        2106
CCC AGT CTT GCT TCT CGC TAT TAC AAA AGG CTA TGT CTG GCT ATT CTA CCA CGG
```

FIGURE 1F

```
       2115      2124      2133      2142      2151      2160
AGA CTC TGC CGT TCC TTG TTT AAG CGG TTA CCT ATA ATG CTG AGC CTC TTA GAA 2169      2178      2187      2196      2205      2214
CCA GTA CAA AAG TTC CTA GCA ATT GCA TGT GGA AGG ATT CCC GGA GGT CAA TCT 2223      2232      2241      2250      2259      2268
TGC CTT TAC CCC AAT TCT TAA GCT TGG AAC CTT TTC ACC TGT TTG GCT AAT TCT 2277      2286      2295
CCC GGC GGG TTT CCC CCA CGC TGT AAA GGT 3'
```

FIGURE 1G

|       |                                              | |
|-------|----------------------------------------------|---|
| 1     | M A P S G L K A V V G E K I L S G V I R S V K K D G E W K V L I M D H P S M R I | NVTP-1 |
| 1     | M A P L G L K A V V G E K I L S G V I R S V K K D G E W K V L I M D H P S M R I | g642026 |
| 1     | M A P S G L K E V V G E K I L N G V I R S V K K D G E W K V L I M D H P S M R I | g1246217 |
| 41    | L S S C C K M S D I L A E G I T I V E D I N K R R E P I P S L E A I Y L L S P T | NVTP-1 |
| 41    | L S S C C K M S D I L A E G I T I V E D I N K R R E P I P S L E A I Y L L S P T | g642026 |
| 41    | L S S C C K M S D I L A E G I T I V E D I N K R R E P I P S L E A I Y L L S P T | g1246217 |
| 81    | E K S V Q A L I K D F Q G T P T F T Y K A A H I F F T D T C P E P L F S E L G R | NVTP-1 |
| 81    | E K S V Q A L I A D F Q G T P T F T Y K A A H I F F T D T C P E P L F S E L G R | g642026 |
| 81    | E K S V Q A L I A D F R G T P T F T Y K A A H I F F T D T C P E P L F T E L S R | g1246217 |
| 121   | S R L A K V V K T L K E I H L A F L P Y E A Q V F S L D A P H S T Y N L Y C P F | NVTP-1 |
| 121   | S R L A K A V K T L K E I H L A F L P Y E A Q V F S L D A P H S T Y N L Y C P F | g642026 |
| 121   | S R L A K V V K T L K E I H L A F L P Y E A Q V F S L D A P H S T Y N L Y C P F | g1246217 |
| 161   | R A E E R T R Q L E V L A Q Q I A T L C A T L Q E Y P A I R Y R K G P E D T A Q | NVTP-1 |
| 161   | R A G E R G R Q L D A L A Q Q I A T L C A T L Q E Y P S I R Y R K G P E D T A Q | g642026 |
| 161   | R V G E R A R Q I E A L A Q Q I A T L C A T L Q E Y P A I R Y R K G P E V T A Q | g1246217 |

FIGURE 2A

```
201  L A H A V L A K L N A F K A D T P S L G E G P E K T R S Q L L I M D R A A D P V   NVTP-1
201  L A H A V L A K L N A F K A D T P S L G E G P E K T R S Q L L I M D R A A D P V   g642026
201  L A N A V L A K L N A F K A D N P S L G E G P E K T R S Q L L I V D R G A D P V   g1246217

241  S P L L H E L T F Q A M A Y D L L D I E Q D T Y R Y E T T G L S E A R E K A V L   NVTP-1
241  S P L L H E L T F Q A M A Y D L L D I E Q D T Y R Y E T T G L S E S R E K A V L   g642026
241  S P L L H E L T F Q A M A Y D L L N I E Q D T Y R Y E T T G L S E A R E K A V L   g1246217

281  L D E D D D L W V E L R H M H I A D V S K K V T E L L R T F C E S K G L T T D K   NVTP-1
281  L D E D D D L W V E L R H M H I A D V S K K V T E L L K T F C E S K R L T T D K   g642026
281  L D E D D D L W V E L R H M H I A D V S K K V T E L L K T F C E S K R L T T D K   g1246217

321  A N I K D L S Q I L K K M P Q Y Q K E L N K Y S T H L H L A D D C M K H F K G S   NVTP-1
321  A N I K D L S H I L K K M P Q Y Q K E L N K Y S T H L H L A D D C M K H F K G S   g642026
321  A N I K D L S H I L K K M P Q Y Q K E L N K Y S T H L H L A D D C M K H F K G S   g1246217

361  V E K L C S V E Q D L A M G S D A E G E K I K D S M K L I V P V L L D A A V P A   NVTP-1
361  V E K L C S V E Q D L A M G S D A E G E K I K D A M K L I V P V L L D A S V P P   g642026
361  V E K L C G V E Q D L A M G S D T E G E K I K D A M K L I V P V L L D A A V P A   g1246217
```

FIGURE 2B

```
401  YDKIRVLLLYILLRNGVSEENLAKLIQHANVQAHSSLIRN    NVTP-1
401  YDKIRVLLLYILLRNGVSEENLAKLIQHANVQSYSSLIRN    g642026
401  YDKIRVLLLYILLRNGVSEENLAKLIQHANVQAHSSLIRN    g1246217

441  LEQLGGTVTNPGGSGTSSRLEPRERMEPTYQLSRWTPVIK    NVTP-1
441  LEQLGGTVTNSAGSGTSSRLERRERMEPTYQLSRWSPVIK    g642026
441  LEQLGGTVTNPGGPGTSSRLERRERLEPTYQLSRWTPVIK    g1246217

481  DVMEDAVEDRLDRNLWPFVSDPAPTASSQAAVSARFGHWH    NVTP-1
481  DVMEDVVEDRLDRKLWPFVSDPAPVPSSQAAVSARFGHWH    g642026
481  DVMEDAVEDRLDRKLWPFVSDPAPTSSSQAAVSARFGHWH    g1246217

521  KNKAGVEARAGPRLIVYVMGGVAMSEMRAAYEVTRATEGK    NVTP-1
521  KNKAGVEARAGPRLIVYIVGGVAMSEMRAAYEVTRATEGK    g642026
521  KNKAGVEMRAGPRLIIYVMGGVAMSEMRAAYEVTRATDGK    g1246217

561  WEVLIGSSHILTPTRFLDDLKALDKKLEDIALP           NVTP-1
561  WEVLIGSSHILTPTRFLDDLKTLDQKLEGVALP           g642026
561  WEVLIGSSHILTPTRFLDDLKTLDQKLEDIALP           g1246217
```

FIGURE 2C

METHOD OF DETECTING A NUCLEIC ACID ENCODING A VESICLE TRANSPORT PROTEIN

This application is a divisional application of U.S. application Ser. No. 08/900,927, filed Jul. 25, 1997, now U.S. Pat. No. 5,840,537.

FIELD OF THE INVENTION

This invention relates to nucleic acid and amino acid sequences of a new vesicle transport protein and to the use of these sequences in the diagnosis, prevention, and treatment of cancer and immune disorders.

BACKGROUND OF THE INVENTION

Vesicle transport is the general process in eukaryotic cells by which proteins synthesized in the endoplasmic reticulum (ER) are transported via the Golgi network to the various compartments in the cell where they will function. Other proteins are transported to the cell surface by this process where they may be secreted (exocytosis). Such proteins include membrane bound receptors or other membrane proteins, neurotransmitters, hormones, and digestive enzymes. The transport process uses a series of transport vesicles that shuttle a protein from one membrane-bound compartment (donor compartment) to another (acceptor compartment) until the protein reaches its proper destination (Rothman, J. E. and Wieland, F. T. et al. (1996) 727:227–33).

The process begins with the budding of a vesicle out of the donor membrane. The vesicle contains the protein to be transported and is surrounded by a protective coat made up of protein subunits recruited from the cytosol. The initial budding process and coating processes are controlled by a cytosolic GTP-binding protein, either SAR or ARF. When GTP binds and activates SAR, it binds to the donor membrane and initiates the vesicle assembly process. The coated vesicle containing the GTP-SAR complex detaches from the donor compartment and is transported through the cytosol. During the transport process, the SAR-bound GTP is hydrolyzed to GDP, and the inactivated SAR dissociates from the transport vesicle. At this point, the protective coat becomes unstable and dissociates from the enclosed vesicle. The uncoated vesicle is recognized by its acceptor compartment through exposed surface identifiers (v-SNAREs) which bind with corresponding molecules on the acceptor compartment membrane (t-SNAREs). The transport process ends when the vesicle fuses with the target membrane.

The fusion of the transport vesicle with the acceptor compartment membrane, that follows the initial binding (or docking) of the two compartments, involves the formation of a complex between the v-SNARE, t-SNARE, and certain other proteins recruited from the cytosol. Many of these other proteins have been identified although their exact functions in the fusion complex remain uncertain (Tellam, J. T. et al. (1995) J. Biol. Chem. 270:5857–63; Hata, Y. and Sudhof, T. C. (1995) J. Biol. Chem. 270:13022–28). N-ethylmaleimide sensitive factor (NSF) and soluble NSF-attachment protein (SNAP) are two such proteins that are conserved from yeast to man and function in most intracellular membrane fusion reactions. Sec1 represents a family of yeast proteins that function at many different stages in the secretory pathway including membrane fusion. Recently, mammalian homologs of Sec 1, called Munc-18 proteins, have been identified (Katagiri, H. et al. (1995) J. Biol. Chem. 270:4963–66; Hata et al. supra). Although Munc-18-1 and Munc-18a were originally found in neural tissue, other isoforms such as Munc-18-2, Munc-18b, and -18c are ubiquitously expressed. Munc-18 proteins specifically bind to a family of t-SNARE proteins known as syntaxins. Like Munc-18, different isoforms of syntaxin are found in different tissues and show specific binding to different Munc-18 isoforms (Hata et al. supra).

Although there is no functional data concerning the role of Munc-18 proteins in vesicle transport, mutations in the gene product of a highly related protein from *Caenorhabditis elegans*, unc-18, results in accumulation of acetylcholine containing secretory vesicles and abnormalities in development of the *C. elegans* nervous system (Tellam et al. supra). Specific functional motifs have yet to be identified in Munc-18 and other related syntaxin-binding proteins. However, studies with various truncated forms of Munc-18 indicate that the entire sequence is required for interaction with syntaxin (Hata et al. supra). Phosphorylation of Munc-18 by protein kinase C is also implicated in regulating interaction with syntaxin (Fujita, Y. et al. (1996) J. Biol. Chem. 271:7265–68).

The discovery of a new vesicle transport protein and the polynucleotides encoding it satisfies a need in the art by providing new compositions which are useful in the diagnosis, prevention and treatment of cancer and immune disorders.

SUMMARY OF THE INVENTION

The invention features a substantially purified polypeptide, vesicle transport protein (NVTP-1), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding NVTP-1 under conditions suitable for the expression of the polypeptide; and b) recovering the polypeptide from the host cell culture.

The invention also provides a pharmaceutical composition comprising a substantially purified NVTP-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still farther, the invention provides a purified agonist of the polypeptide of SEQ ID NO:1.

The invention also provides a method for treating or preventing cancer comprising administering to a subject in need of such treatment an effective amount of purified a antagonist of NVTP-1.

The invention also provides a method for treating or preventing an immune disorder comprising administering to a subject in need of such treatment an effective amount of a purified antagonist of NVTP-1.

The invention also provides a method for detecting a polynucleotide which encodes NVTP-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding NVTP-1 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of NVTP-1. The alignment was produced using MACDNASIS PRO software (Hitachi Software Engineering Co. Ltd. San Bruno, Calif.).

FIGS. 2A, 2B, and 2C show the amino acid sequence alignments among NVTP-1 (SEQ ID NO:1), mouse vesicle transport protein, Munc-18b (GI 642026; SEQ ID NO:3) and a dog Sec1-related vesicle transport protein, Sec1-RVTP (GI 1246217; SEQ ID NO:4), produced using the multisequence alignment program of DNASTAR™ software (DNASTAR Inc, Madison Wis.).

DESCRIPTION OF THE INVENTION

Figure 3A:
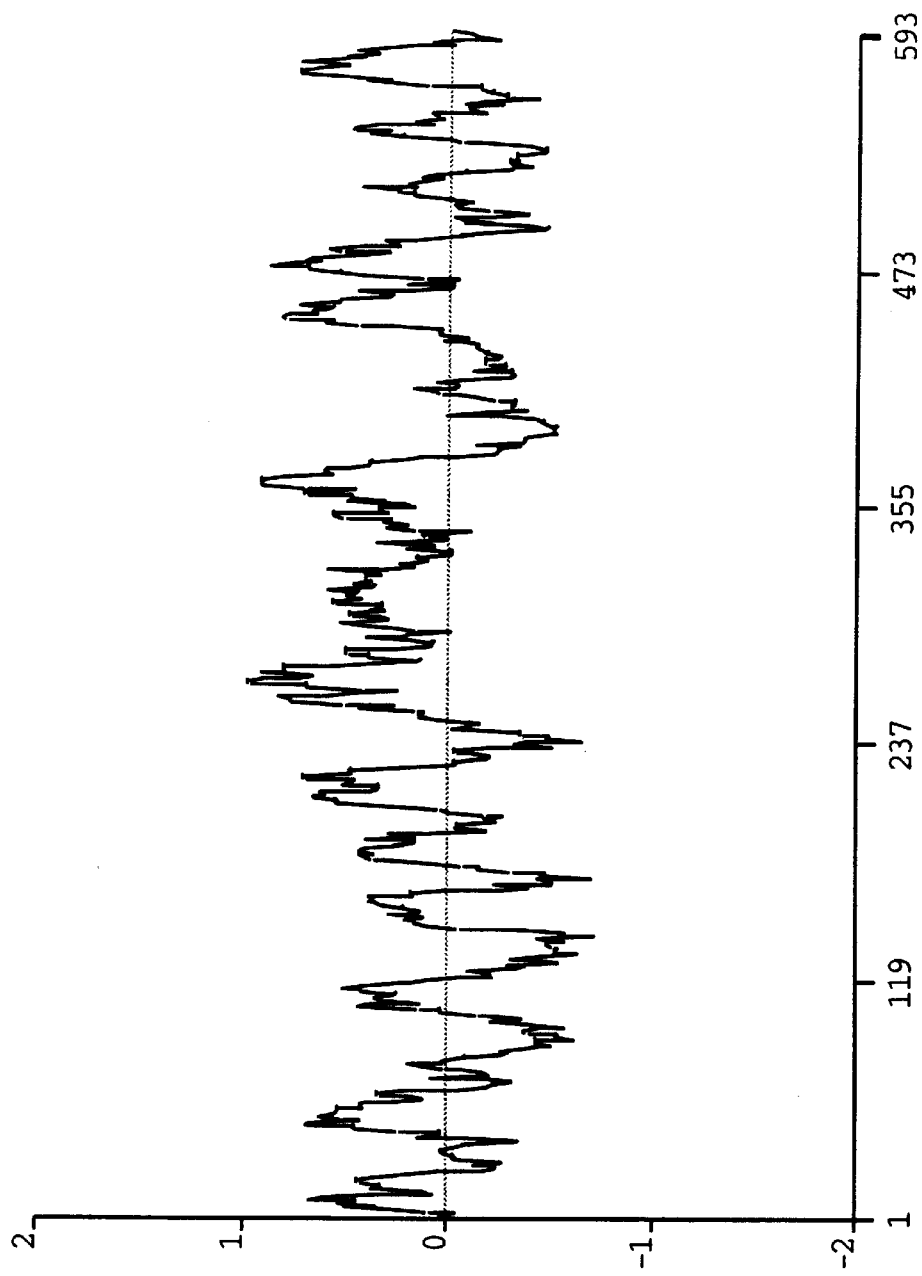
FIGS. 3A, 3B, and 3C show the hydrophobicity plots for NVTP-1 (SEQ ID NO:1), mouse Munc-18b (SEQ ID NO:3), and dog Sec1-RVTP (SEQ ID NO:4), respectively; the positive X axis reflects amino acid position, and the negative Y axis, hydrophobicity (MacDNASIS PRO software).
Figure 3B:
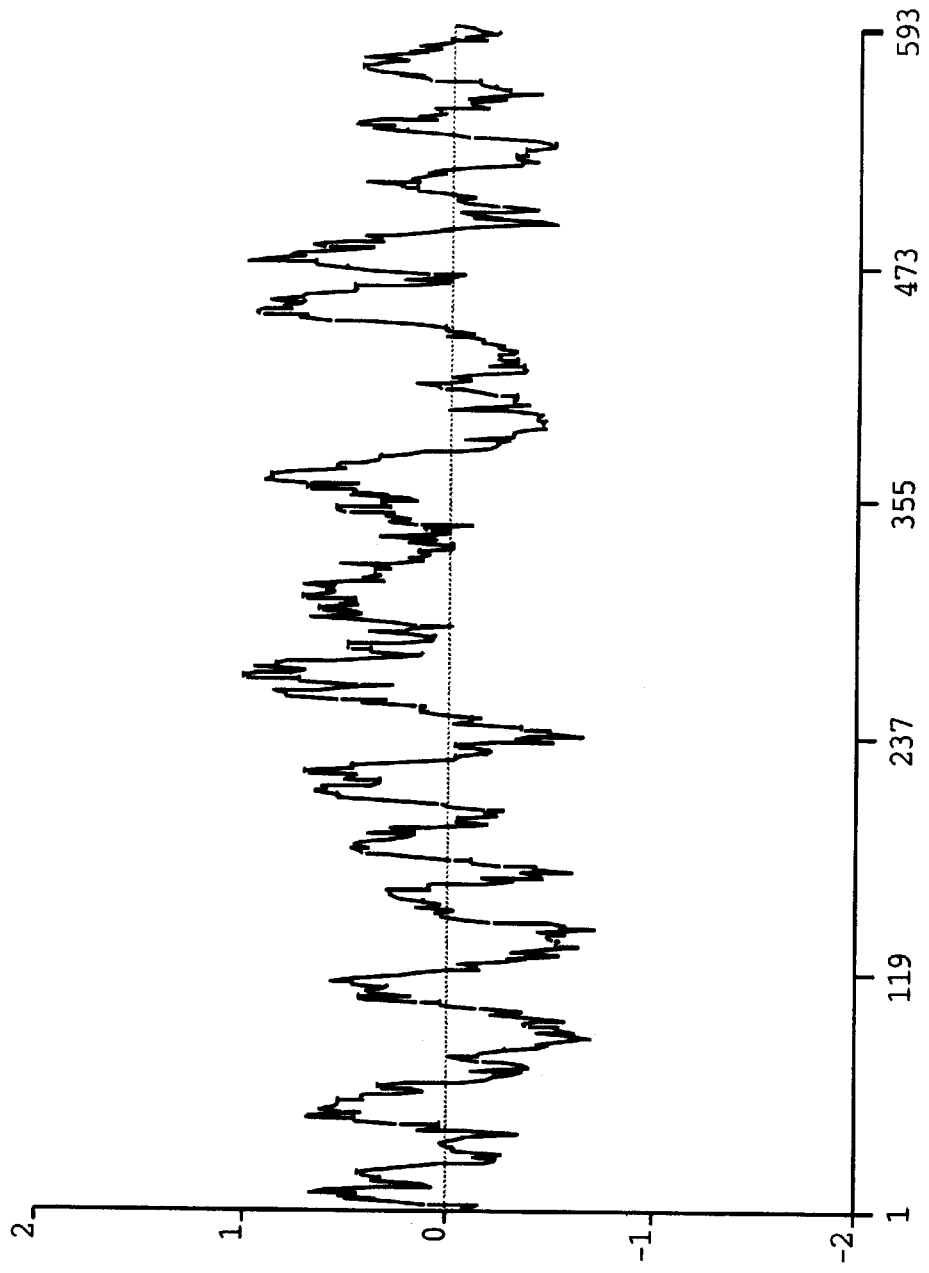
Figure 3C:
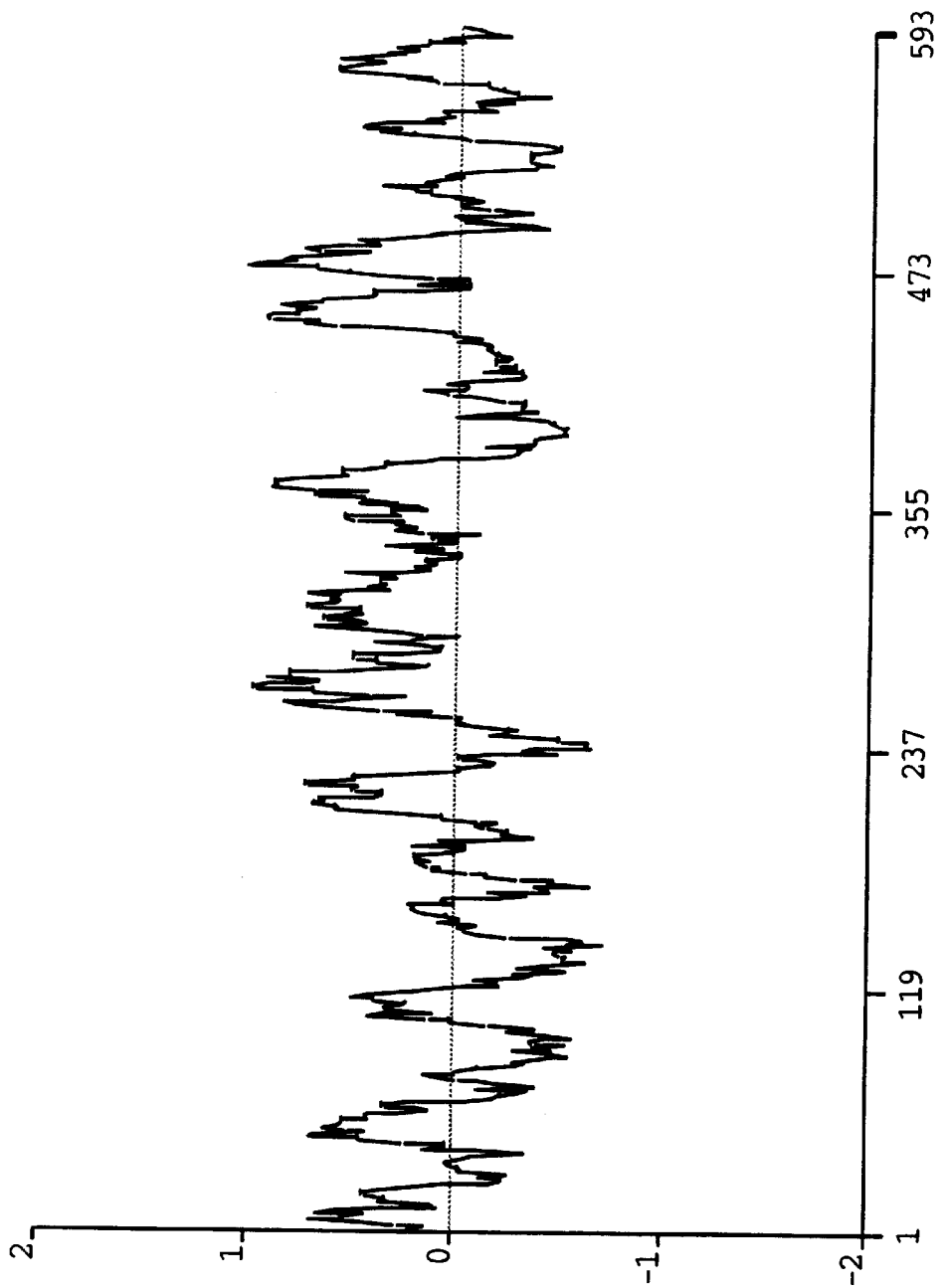

Before the present proteins, nucleotide sequences, and methods are described, it is understood that this invention is not limited to the particular methodology, protocols, cell lines, vectors and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

NVTP-1, as used herein, refers to the amino acid sequences of substantially purified NVTP-1 obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to NVTP-1, increases or prolongs the duration of the effect of NVTP-1. Agonists may include proteins, nucleic acids, carbohydrates, or any other molecules which bind to and modulate the effect of NVTP-1.

An "allele" or "allelic sequence", as used herein, is an alternative form of the gene encoding NVTP-1. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding NVTP-1 as used herein include those with deletions, insertions, or substitutions of different nucleotides resulting in a polynucleotide that encodes the same or a functionally equivalent NVTP-1. Included within this definition are polymorphisms which may or may not be readily detectable using a particular oligonucleotide probe of the polynucleotide encoding NVTP-1, and improper or unexpected hybridization to alleles, with a locus other than the normal chromosomal locus for the polynucleotide sequence encoding NVTP-1. The encoded protein may also be "altered" and contain deletions, insertions, or substitutions of amino acid residues which produce a silent change and result in a functionally equivalent NVTP-1. Deliberate amino acid substitutions may be made on the basis of similarity in polarity, charge, solubility, hydrophobicity, hydrophilicity, and/or the amphipathic nature of the residues as long as the biological or immunological activity of NVTP-1 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of NVTP-1 are preferably about 5 to about 15 amino acids in length and retain the biological activity or the immunological activity of NVTP-1. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "antagonist" as used herein, refers to a molecule which, when bound to NVTP-1, decreases the amount or the duration of the effect of the biological or immunological activity of NVTP-1. Antagonists may include proteins, nucleic acids, carbohydrates, antibodies or any other molecules which decrease the effect of NVTP-1.

As used herein, the term "antibody" refers to intact molecules as well as fragments thereof, such as Fa, F(ab')$_2$, and Fv, which are capable of binding the epitopic determinant. Antibodies that bind NVTP-1 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic NVTP-1, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein, refers broadly to any composition containing the given polynucleotide sequence. The composition may comprise a dry formulation or an aqueous solution. Compositions comprising polynucleotide sequences encoding NVTP-1 (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding NVTP-1 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to NVTP-1 or the encoded NVTP-1. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10 M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of NVTP-1. For example, modulation may cause an increase or a decrease in protein activity, binding characteristics, or any other biological, functional or immunological properties of NVTP-1.

"Nucleic acid sequence" as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the fill-length NVTP-1 and fragments thereof.

The term "sample", as used herein, is used in its broadest sense. A biological sample suspected of containing nucleic acid encoding NVTP-1, or fragments thereof, or NVTP-1 itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of NVTP-1, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human vesicle transport protein (hereinafter referred to as "NVTP-1"), the polynucleotides encoding NVTP-1, and the use of these compositions for the diagnosis, prevention, or treatment of cancer and immune disorders.

Nucleic acids encoding the NVTP-1 of the present invention were first identified in Incyte Clone 475485 from the peripheral blood macrophage cDNA library (MMLR2DT01) using a computer search for amino acid sequence alignments. A consensus sequence, SEQ ID NO:2, was derived from the following overlapping and/or extended nucleic acid sequences: Incyte Clones 464199/LATRNOT01, 475485/MMLR2DT01, 757177/BRAITUT02, 1335214/COLNNOT13, 1449949/PLACNOT02, and 1561234/SPLNNOT04.

In one embodiment, the invention encompasses a polypeptide comprising the amino acid sequence of SEQ ID NO:1, as shown in FIG. 1. NVTP-1 is 593 amino acids in length and has numerous potential protein kinase C phosphorylation sites at residue(s) $S_{21}$, $S_{37}$, $T_{80}$, $T_{98}$, $T_{129}$, $T_{263}$, $S_{300}$, $T_{318}$, $S_{385}$, $S_{457}$, and $S_{513}$. A potential protein tyrosine kinase phosphorylation site is found at $Y_{470}$. Cysteine residues at $C_{44}$, $C_{45}$, $C_{110}$, $C_{158}$, $C_{180}$, $C_{311}$, $C_{353}$, and $C_{365}$ represent potential intramolecular cysteine disulfide bridging sites. As shown in FIG. 2, NVTP-1 has chemical and structural homology with mouse Munc-18b (GI 642026; SEQ ID NO:3) and dog Sec1-RVTP (GI 1246217; SEQ ID NO:4). In particular, NVTP-1 shares 95% identity with both Munc-18b and Sec1-RVTP. All but one ($S_{385}$) of the eleven potential protein kinase C phosphorylation sites in NVTP-1 are found in both Munc-18b and Sec1-RVTP. The tyrosine kinase phosphorylation site at $Y_{470}$ and the eight cysteine residues found in NVTP-1 are also found in Munc-18b and Sec1-RVTP. As illustrated by FIGS. 3A, 3B, and 3C, NVTP-1, Munc-18b and Sec1-RVTP have rather similar hydrophobicity plots. Northern analysis shows the expression of this sequence in various libraries, at least 45% of which are immortalized or cancerous and at least 35% of which involve inflammation or the immune response. Of particular note is the expression of NVTP-1 in inflammatory conditions including Crohn's disease, ulcerative colitis, and asthma.

The invention also encompasses NVTP-1 variants. A preferred NVTP-1 variant is one having at least 80%, and more preferably at least 90%, amino acid sequence identity to the NVTP-1 amino acid sequence (SEQ ID NO:1) and which retains at least one biological, immunological or other functional characteristic or activity of NVTP-1. A most preferred NVTP-1 variant is one having at least 95% amino acid sequence identity to SEQ ID NO:1.

The invention also encompasses polynucleotides which encode NVTP-1. Accordingly, any nucleic acid sequence which encodes the amino acid sequence of NVTP-1 can be used to produce recombinant molecules which express NVTP-1. In a particular embodiment, the invention encompasses the polynucleotide comprising the nucleic acid sequence of SEQ ID NO:2 as shown in FIGS. 1A, 1B, 1C, 1D, 1E, 1F, and 1G.

It will be appreciated by those skilled in the art that as a result of the degeneracy of the genetic code, a multitude of nucleotide sequences encoding NVTP-1, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NVTP-1, and all such variations are to be considered as being specifically disclosed.

Although nucleotide sequences which encode NVTP-1 and its variants are preferably capable of hybridizing to the nucleotide sequence of the naturally occurring NVTP-1 under appropriately selected conditions of stringency, it may be advantageous to produce nucleotide sequences encoding NVTP-1 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NVTP-1 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode NVTP-1 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding NVTP-1 or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton MICROLAB 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding NVTP-1 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NVTP-1 may be used in recombinant DNA molecules to direct expression of NVTP-1, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express NVTP-1.

As will be understood by those of skill in the art, it may be advantageous to produce NVTP-1-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter NVTP-1 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding NVTP-1 may be ligated to a heterologous sequence to encode a fusion protein. For example, to screen peptide libraries for inhibitors of NVTP-1 activity, it may be useful to encode a chimeric NVTP-1 protein that can be recognized by a commercially available antibody. A fusion protein may also be engineered to contain a cleavage site located between the NVTP-1 encoding sequence and the heterologous protein sequence, so that NVTP-1 may be cleaved and purified away from the heterologous moiety.

In another embodiment, sequences encoding NVTP-1 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of NVTP-1, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of NVTP-1, or any part thereof, may be altered during direct synthesis and/or combined using chemical methods with sequences from other proteins, or any part thereof, to produce a variant polypeptide.

In order to express a biologically active NVTP-1, the nucleotide sequences encoding NVTP-1 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding NVTP-1 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding NVTP-1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NVTP-1, vectors based on SV40 or EBV may be used with an appropriate selectable marker.

In bacterial systems, a number of expression vectors may be selected depending upon the use intended for NVTP-1. For example, when large quantities of NVTP-1 are needed for the induction of antibodies, vectors which direct high level expression of fusion proteins that are readily purified may be used. Such vectors include, but are not limited to, the multifinctional *E. coli* cloning and expression vectors such as BLUESRIPT (Stratagene), in which the sequence encoding NVTP-1 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding NVTP-1 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express NVTP-1. For example, in one such system, *Autographa californica* nuclear polyhedrosis virus (AcNPV) is used as a vector to express foreign genes in *Spodoptera frugiperda* cells or in Trichoplusia larvae. The sequences encoding NVTP-1 may be cloned into a non-essential region of the virus, such as the polyhedrin gene, and placed under control of the polyhedrin promoter. Successful insertion of NVTP-1 will render the polyhedrin gene inactive and produce recombinant virus lacking coat protein. The recombinant viruses may then be used to infect, for example, *S. frugiperda* cells or Trichoplusia larvae in which NVTP-1 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding NVTP-1 may be ligated into an adenovirus transcription/translation complex consisting of the late promoter and tripartite leader sequence. Insertion in a non-essential E1 or E3 region of the viral genome may be used to obtain a viable virus which is capable of expressing NVTP-1 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding NVTP-1. Such signals include the ATG initiation codon and adjacent sequences. In cases where sequences encoding NVTP-1, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express NVTP-1 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding NVTP-1 is inserted within a marker gene sequence, transformed cells containing sequences encoding NVTP-1 can be identified by the absence of marker gene function. Alternatively, a marker gene can be placed in tandem with a sequence encoding NVTP-1 under the control of a single promoter. Expression of the marker gene in response to induction or selection usually indicates expression of the tandem gene as well.

Alternatively, host cells which contain the nucleic acid sequence encoding NVTP-1 and express NVTP-1 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding NVTP-1 can be detected by DNA-DNA or DNA-RNA hybridization or amplification using probes or fragments or fragments of polynucleotides encoding NVTP-1. Nucleic acid amplification based assays involve the use of oligonucleotides or oligomers based on the sequences encoding NVTP-1 to detect transformants containing DNA or RNA encoding NVTP-1.

A variety of protocols for detecting and measuring the expression of NVTP-1, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NVTP-1 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NVTP-1 include oligolabeling, nick translation, end-labeling or PCR amplification using a labeled nucleotide. Alternatively, the sequences encoding NVTP-1, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding NVTP-1 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode NVTP-1 may be designed to contain signal sequences which direct secretion of NVTP-1 through a prokaryotic or eukaryotic cell membrane. Other constructions may be used to join sequences encoding NVTP-1 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (immunex Corp., Seattle, Wash.). The inclusion of cleavable linker sequences such as those specific for Factor XA or enterokinase (Invitrogen, San Diego, Calif.) between the purification domain and NVTP-1 may be used to facilitate purification. One such expression vector provides for expression of a fusion protein containing NVTP-1 and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying NVTP-1 from the fusion protein. A discussion of vectors which contain fusion proteins is provided in Kroll, D. J. et al. (1993; DNA Cell Biol. 12:441–453).

In addition to recombinant production, fragments of NVTP-1 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of NVTP-1 may be chemically synthesized separately and combined using chemical methods to produce the full length molecule.

THERAPEUTICS

Chemical and structural homology exists between/among NVTP-1 and vesicle transport proteins from mouse (GI 642026) and dog (GI 1246217). In addition, NVTP-1 is expressed in cancerous tissues and tissues associated with inflammation and the immune response. Therefore, NVTP-1 appears to play a role in cancer and immune disorders. In particular, increased activity or expression of NVTP-1 appears to be associated with cancer and immune disorders.

Therefore, in one embodiment, an antagonist of NVTP-1 may be administered to a subject to prevent or treat cancer. Cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds NVTP-1 may be used directly as an antagonist or indirectly as a targeting or delivery mechanism for bringing a pharmaceutical agent to cells or tissue which express NVTP-1.

In another embodiment, an antagonist of NVTP-1 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding NVTP-1 may be administered to a subject to treat or prevent any cancer including, but not limited to, the types of cancer described above.

In another embodiment, a vector expressing the complement of the polynucleotide encoding NVTP-1 may be administered to a subject to treat or prevent an immune disorder including, but not limited to, any of the immune disorders described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of NVTP-1 may be produced using methods which are generally known in the art. In particular, purified NVTP-1 may be used to produce antibodies or to screen libraries of pharmaceutical agents to identify those which specifically bind NVTP-1.

Antibodies to NVTP-1 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with NVTP-1 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to NVTP-1 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of NVTP-1 amino acids may be fused with those of another protein such as keyhole limpet hemocyanin and antibody produced against the chimeric molecule.

Monoclonal antibodies to NVTP-1 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce NVTP-1-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for NVTP-1 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NVTP-1 and its specific antibody. A two-site, monoclonal-based immunoassay utilizing monoclonal antibodies reactive to two non-interfering NVTP-1 epitopes is preferred, but a competitive binding assay may also be employed (Maddox, supra).

In another embodiment of the invention, the polynucleotides encoding NVTP-1, or any fragment or complement thereof, may be used for therapeutic purposes. In one aspect, the complement of the polynucleotide encoding NVTP-1 may be used in situations in which it would be desirable to block the transcription of the mRNA. In particular, cells may be transformed with sequences complementary to polynucleotides encoding NVTP-1. Thus, complementary molecules or fragments may be used to modulate NVTP-1 activity, or to achieve regulation of gene function. Such technology is now well known in the art, and sense or antisense oligonucleotides or larger fragments, can be designed from various locations along the coding or control regions of sequences encoding NVTP-1.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding NVTP-1. These techniques are described both in Sambrook et al. (supra) and in Ausubel et al. (supra).

Genes encoding NVTP-1 can be turned off by transforming a cell or tissue with expression vectors which express high levels of a polynucleotide or fragment thereof which encodes NVTP-1. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding NVTP-1 (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NVTP-1.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NVTP-1. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NVTP-1, antibodies to NVTP-1, mimetics, agonists, antagonists, or inhibitors of NVTP-1. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for to ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NVTP-1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NVTP-1 or fragments thereof, antibodies of NVTP-1, agonists, antagonists or inhibitors of NVTP-1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind NVTP-1 may be used for the diagnosis of conditions or diseases characterized by expression of NVTP-1, or in assays to monitor patients being treated with NVTP-1, agonists, antagonists or inhibitors. The antibodies useful for diagnostic purposes may be prepared in the same manner as those described above for therapeutics. Diagnostic assays for NVTP-1 include methods which utilize the antibody and a label to detect NVTP-1 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NVTP-1 are known in the art and provide a basis for diagnosing altered or abnormal levels of NVTP-1 expression. Normal or standard values for NVTP-1 expression are established by combining body fluids or cell extracts taken from normal mammalian subjects, preferably human, with antibody to NVTP-1 under conditions suitable for complex formation. The amount of standard complex formation may be quantified by various methods, but preferably by photometric means. Quantities of NVTP-1 expressed in subject, control, and disease samples from biopsied tissues are compared with the standard values. Deviation between standard and subject values establishes the parameters for diagnosing disease.

In another embodiment of the invention, the polynucleotides encoding NVTP-1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of NVTP-1 may be correlated with disease. The diagnostic assay may be used to distinguish between absence, presence, and excess expression of NVTP-1, and to monitor regulation of NVTP-1 levels during therapeutic intervention.

In one aspect, hybridization with PCR probes which are capable of detecting polynucleotide sequences, including genomic sequences, encoding NVTP-1 or closely related molecules, may be used to identify nucleic acid sequences which encode NVTP-1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NVTP-1, alleles, or related sequences.

Probes may also be used for the detection of related sequences, and should preferably contain at least 50% of the nucleotides from any of the NVTP-1 encoding sequences. The hybridization probes of the subject invention may be DNA or RNA and derived from the nucleotide sequence of SEQ ID NO:2 or from genomic sequence including promoter, enhancer elements, and introns of the naturally occurring NVTP-1.

Means for producing specific hybridization probes for DNAs encoding NVTP-1 include the cloning of nucleic acid sequences encoding NVTP-1 or NVTP-1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin biotin coupling systems, and the like.

Polynucleotide sequences encoding NVTP-1 may be used for the diagnosis of conditions or disorders which are associated with expression of NVTP-1. Examples of such conditions or disorders include cancer such as cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. The polynucleotide sequences encoding NVTP-1 may be used in Southern or northern analysis, dot blot, or other membrane-based technologies; in PCR technologies; or in dipstick, pin, ELISA assays or microarrays utilizing fluids or tissues from patient biopsies to detect altered NVTP-1 expression. Such qualitative or quantitative methods are well known in the art.

In a particular aspect, the nucleotide sequences encoding NVTP-1 may be useful in assays that detect activation or induction of various cancers, particularly those mentioned above. The nucleotide sequences encoding NVTP-1 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NVTP-1 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NVTP-1, a normal or standard profile for expression is established. This may be accomplished by combining body fluids or cell extracts taken from normal subjects, either animal or human, with a sequence, or a fragment thereof, which encodes NVTP-1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professional to employ preventative measures or aggressive treatment earlier thereby preventing the development or further progression of the cancer.

Additional diagnostic uses for oligonucleotides designed from the sequences encoding NVTP-1 may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NVTP-1 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide. sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode NVTP-1 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding NVTP-1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NVTP-1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NVTP-1 and the agent being tested, may be measured.

Another technique for drug screening which may be used provides for high throughput screening of compounds having suitable binding affinity to the protein of interest as described in published PCT application WO84/03564. In this method, as applied to NVTP-1 large numbers of different small test compounds are synthesized on a solid substrate, such as plastic pins or some other surface. The test compounds are reacted with NVTP-1, or fragments thereof, and washed. Bound NVTP-1 is then detected by methods well known in the art. Purified NVTP-1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NVTP-1 specifically compete with a test compound for binding NVTP-1. In this manner, the antibodies can be used to detect the presence of any peptide which shares one or more antigenic determinants with NVTP-1.

In additional embodiments, the nucleotide sequences which encode NVTP-1 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I MMLR2DT01 cDNA Library Construction

The MMLR2DT01 cDNA library was constructed from normal peripheral blood macrophages obtained from two 24 year old, Caucasian males. This library represents a mixture of allogeneically stimulated human macrophage populations obtained from Ficoll/Hypaque purified buffy coats. The cells from the two donors (not typed for HLA alleles) were incubated at a density of $1\times10^6$/ml, cultured for 48 hours in DME containing 10% human serum.

After incubation, macrophages mostly adhered to the plastic surface of the petri dish, whereas most other cell types, B and T lymphocytes, remained in solution. The DME was decanted from the wells and the wells were washed with phosphate buffered saline (PBS). Macrophages were released from the plastic surface by gently scraping the petri dishes in PBS/1 mM EDTA. Macrophages were lysed immediately in buffer containing guanidinium isothiocyanate. It must be noted that some contaminating T and B lymphocytes may also have been present.

The lysate was extracted twice with a mixture of phenol and chloroform, pH 8.0, and centrifuged over a CsCl cushion using a Beckman SW28 rotor in a L8-70M Ultracentrifuge (Beckman Instruments). The RNA was precipitated using 0.3 M sodium acetate and 2.5 volumes of ethanol, resuspended in water and DNase treated for 15 min at 37° C. The total RNA was isolated using the QIAGEN OLIGOTEX kit (Qiagen Inc., Chatsworth Calif.).

The poly $A^+$RNA was used in the SuperScript Plasmid System for cDNA Synthesis and Plasmid Cloning (catalogue #18248-013; Gibco\BRL) with the recommended protocol. cDNAs were fractionated on a SEPHAROSE CL4B column (catalog #275105, Pharmacia, and those cDNAs exceeding 400 bp were ligated into the PSPORT1 plasmid. The plasmid was transformed into chemically competent DH5α host cells (Gibco\BRL).

II Isolation and Sequencing of cDNA Clones

Plasmid DNA was released from the cells and purified using the Miniprep Kit (Catalogue # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, Gibco\BRL) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton MICROLAB 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J.Mol.Evol.* 36:290–300; Altschul, S. F. et al. (1990) *J.Mol.Evol.* 215:403–410) are used to search for identical or related molecules in nucleotide databases such as GenBank or the LIFESEQ® database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding NVTP-1 occurs. Abundance and percent abundance are also reported. Abundance directly reflects the number of times a particular transcript is represented in a cDNA library, and percent abundance is abundance divided by the total number of sequences examined in the cDNA library.

V Extension of NVTP-1 Encoding Polynucleotides

The nucleic acid sequence of the Incyte Clone 475485 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72 C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent *E. coli* cells (in 40 μl of appropriate media) were transformed with 3 μl of ligation mixture and cultured in 80 μl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing 10$^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the NVTP-1-encoding sequence, or any part thereof, is used to decrease or inhibit expression of naturally occurring NVTP-1. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of NVTP-1, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the NVTP-1-encoding transcript.

IX Expression of NVTP-1

Expression of NVTP-1 is accomplished by subcloning the cDNAs into appropriate vectors and transforming the vectors into host cells. In this case, the cloning vector is also used to express NVTP-1 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of NVTP-1 into the bacterial growth media which can be used directly in the following assay for activity.

X Demonstration of NVTP-1 Activity

NVTP-1 activity may be demonstrated by the binding of NVTP-1 to syntaxin using an in vitro assay (Ravichandran, V. et al. (1996) J. Biol. Chem. 271:13300–03). NVTP-1 is radiolabeled with $^{35}$S, and a syntaxin binding substrate is prepared in the form of a glutathione S-transferase (GST)-syntaxin fusion protein. For each assay, approximately 2 $\mu$g of GST-syntaxin fusion protein absorbed to glutathione-agarose beads is incubated with varying amounts of $^{35}$S-labeled NVTP-1 in a suitable buffer for 3 hours at 4° C. The agarose beads are separated from the incubation by sedimentation and washed several times to remove unbound protein. NVTP-1 and other bound proteins are solubilized from the agarose beads by boiling in wash buffer and separated by SDS-polyacrylamide gel electrophoresis. NVTP-1 is visualized by autoradiography. The amount of radioactivity recovered is proportional to the activity of NVTP-1 in the assay.

XI Production of NVTP-1 Specific Antibodies

NVTP-1 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring NVTP-1 Using Specific Antibodies Naturally occurring or recombinant NVTP-1 is substantially purified by immunoaffinity chromatography using antibodies specific for NVTP-1. An immunoaffinity column is constructed by covalently coupling NVTP-1 antibody to an activated chromatographic resin, such as CNBr-activated SEPHAROSE (Pharmacia & Upjohn). After the coupling, the resin is blocked and washed according to the manufacturer's instructions.

Media containing NVTP-1 is passed over the immunoaffinity column, and the column is washed under conditions that allow the preferential absorbance of NVTP-1 (e.g., high ionic strength buffers in the presence of detergent). The column is eluted under conditions that disrupt antibody/NVTP-1 binding (eg, a buffer of pH 2–3 or a high concentration of a chaotrope, such as urea or thiocyanate ion), and NVTP-1 is collected.

XIII Identification of Molecules Which Interact with NVTP-1

NVTP-1 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled NVTP-1, washed and any wells with labeled NVTP-1 complex are assayed. Data obtained using different concentrations of NVTP-1 are used to calculate values for the number, affinity, and association of NVTP-1 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. A method for detecting a polynucleotide which encodes a vesicle transport protein in a biological sample comprising the steps of:
   a) hybridizing the complement of a polynucleotide encoding SEQ ID NO:1 to nucleic acid material of a biological sample, thereby forming a hybridization complex;
   b) removing non-specific signals from said hybridization complex by sequentially washing at increasing stringency conditions; and
   c) detecting said hybridization complex, wherein the presence of said complex correlates with the presence of a polynucleotide encoding a vesicle transport protein in said biological sample.

2. The method of claim 1 wherein the nucleic acid material is amplified by the polymerase chain reaction prior to hybridization.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 593 amino acids
      (B) TYPE: amino acid
      (C) STRANDEDNESS: single
      (D) TOPOLOGY: linear (vii) IMMEDIATE SOURCE:
      (A) LIBRARY: MMLR20T01
      (B) CLONE: 475485

(xi) SEQUENCE DESCRIPTION: SEQ ID NO:1:

```
Met Ala Pro Ser Gly Leu Lys Ala Val Val Gly Glu Lys Ile Leu Ser
1               5                   10                  15

Gly Val Ile Arg Ser Val Lys Lys Asp Gly Glu Trp Lys Val Leu Ile
                20                  25                  30

Met Asp His Pro Ser Met Arg Ile Leu Ser Ser Cys Cys Lys Met Ser
            35                  40                  45

Asp Ile Leu Ala Glu Gly Ile Thr Ile Val Glu Asp Ile Asn Lys Arg
        50                  55                  60

Arg Glu Pro Ile Pro Ser Leu Glu Ala Ile Tyr Leu Leu Ser Pro Thr
65                  70                  75                  80

Glu Lys Ser Val Gln Ala Leu Ile Lys Asp Phe Gln Gly Thr Pro Thr
                85                  90                  95

Phe Thr Tyr Lys Ala Ala His Ile Phe Phe Thr Asp Thr Cys Pro Glu
                100                 105                 110

Pro Leu Phe Ser Glu Leu Gly Arg Ser Arg Leu Ala Lys Val Val Lys
            115                 120                 125

Thr Leu Lys Glu Ile His Leu Ala Phe Leu Pro Tyr Glu Ala Gln Val
        130                 135                 140

Phe Ser Leu Asp Ala Pro His Ser Thr Tyr Asn Leu Tyr Cys Pro Phe
145                 150                 155                 160
```

-continued

```
Arg Ala Glu Glu Arg Thr Arg Gln Leu Glu Val Leu Ala Gln Gln Ile
                165                 170                 175
Ala Thr Leu Cys Ala Thr Leu Gln Glu Tyr Pro Ala Ile Arg Tyr Arg
                180                 185                 190
Lys Gly Pro Glu Asp Thr Ala Gln Leu Ala His Ala Val Leu Ala Lys
                195                 200                 205
Leu Asn Ala Phe Lys Ala Asp Thr Pro Ser Leu Gly Glu Gly Pro Glu
    210                 215                 220
Lys Thr Arg Ser Gln Leu Leu Ile Met Asp Arg Ala Ala Asp Pro Val
225                 230                 235                 240
Ser Pro Leu Leu His Glu Leu Thr Phe Gln Ala Met Ala Tyr Asp Leu
                245                 250                 255
Leu Asp Ile Glu Gln Asp Thr Tyr Arg Tyr Glu Thr Thr Gly Leu Ser
                260                 265                 270
Glu Ala Arg Glu Lys Ala Val Leu Leu Asp Glu Asp Asp Leu Trp
                275                 280                 285
Val Glu Leu Arg His Met His Ile Ala Asp Val Ser Lys Lys Val Thr
    290                 295                 300
Glu Leu Leu Arg Thr Phe Cys Glu Ser Lys Gly Leu Thr Thr Asp Lys
305                 310                 315                 320
Ala Asn Ile Lys Asp Leu Ser Gln Ile Leu Lys Lys Met Pro Gln Tyr
                325                 330                 335
Gln Lys Glu Leu Asn Lys Tyr Ser Thr His Leu His Leu Ala Asp Asp
                340                 345                 350
Cys Met Lys His Phe Lys Gly Ser Val Glu Lys Leu Cys Ser Val Glu
                355                 360                 365
Gln Asp Leu Ala Met Gly Ser Asp Ala Glu Gly Glu Lys Ile Lys Asp
    370                 375                 380
Ser Met Lys Leu Ile Val Pro Val Leu Leu Asp Ala Ala Val Pro Ala
385                 390                 395                 400
Tyr Asp Lys Ile Arg Val Leu Leu Tyr Ile Leu Leu Arg Asn Gly
                405                 410                 415
Val Ser Glu Glu Asn Leu Ala Lys Leu Ile Gln His Ala Asn Val Gln
                420                 425                 430
Ala His Ser Ser Leu Ile Arg Asn Leu Glu Gln Leu Gly Gly Thr Val
    435                 440                 445
Thr Asn Pro Gly Gly Ser Gly Thr Ser Ser Arg Leu Glu Pro Arg Glu
450                 455                 460
Arg Met Glu Pro Thr Tyr Gln Leu Ser Arg Trp Thr Pro Val Ile Lys
465                 470                 475                 480
Asp Val Met Glu Asp Ala Val Glu Asp Arg Leu Asp Arg Asn Leu Trp
                485                 490                 495
Pro Phe Val Ser Asp Pro Ala Pro Thr Ala Ser Ser Gln Ala Ala Val
                500                 505                 510
Ser Ala Arg Phe Gly His Trp His Lys Asn Lys Ala Gly Val Glu Ala
    515                 520                 525
Arg Ala Gly Pro Arg Leu Ile Val Tyr Val Met Gly Gly Val Ala Met
    530                 535                 540
Ser Glu Met Arg Ala Ala Tyr Glu Val Thr Arg Ala Thr Glu Gly Lys
545                 550                 555                 560
Trp Glu Val Leu Ile Gly Ser Ser His Ile Leu Thr Pro Thr Arg Phe
                565                 570                 575
Leu Asp Asp Leu Lys Ala Leu Asp Lys Lys Leu Glu Asp Ile Ala Leu
                580                 585                 590
```

Pro (2) INFORMATION FOR SEQ ID NO:2:

(i) SEQUENCE CHARACTERISTICS:
        (A) LENGTH: 2297 base pairs
        (B) TYPE: nucleic acid
        (C) STRANDEDNESS: single
        (D) TOPOLOGY: linear (vii) IMMEDIATE SOURCE:
        (A) LIBRARY: MMLR20T01
        (B) CLONE: 475485

(xi) SEQUENCE DESCRIPTION: SEQ ID NO:2:

```
GGCGGCGCCC CTCGGGGAAG ATGGCGCCCT CGGGGCTGAA GGCGGTGGTG GGGGAAAAAA    60
TTCTGAGCGG AGTTATTCGG AGTGTCAAGA AGGATGGGGA GTGGAAGGTG CTTATCATGG   120
ATCACCCAAG CATGCGCATC TTGTCTTCCT GCTGCAAAAT GTCAGATATC CTGGCTGAGG   180
GCATCACCAT TGTTGAAGAC ATCAACAAAC GGCGGGAACC CATTCCCAGT CTGGAGGCCA   240
TTTATTTGCT GAGCCCCACG GAGAAGTCGG TTCAGGCCCT GATCAAAGAC TTCCAGGGGA   300
CCCCGACTTT CACCTACAAA GCGGCCCATA TCTTCTTCAC CGACACCTGC CCCGAGCCCC   360
TGTTCAGTGA GCTAGGCCGC TCTCGTCTGG CAAAGGTGG GAAGACGTTG AAGGAGATTC    420
ACCTTGCCTT CCTCCCCTAC GAGGCCCAGG TGTTCTCCCT CGATGCTCCC CACAGCACCT   480
ACAACCTCTA CTGCCCCTTC CGGGCAGAGG AGCGCACGCG GCAGCTCGAG GTGCTGGCCC   540
AGCAGATTGC CACGCTGTGC GCCACCCTGC AGGAGTACCC GGCCATCCGC TACCGCAAGG   600
GCCCAGAGGA CACAGCCCAG TTGGCCCACG CCGTCCTGGC CAAGCTGAAC GCCTTCAAGG   660
CAGACACTCC CAGTCTGGGC GAGGGCCCAG AGAAAACCCG CTCCCAGCTG CTGATAATGG   720
ACCGGGCAGC TGACCCCGTG TCCCCACTAC TGCATGAGCT CACGTTCCAG GCCATGGCGT   780
ATGATCTGCT GGACATAGAG CAGGACACAT ACAGGTATGA GACCACCGGG CTGAGCGAGG   840
CGCGGGAGAA GGCCGTCTTG CTGGACGAGG ACGATGACTT GTGGGTGGAG CTTCGCCACA   900
TGCATATCGC AGATGTGTCC AAGAAGGTCA CGGAGCTCCT GAGGACCTTC TGTGAGAGCA   960
AGGGGCTGAC CACGGACAAG GCGAACATCA AAGACCTATC CCAGATCCTG AAAAAGATGC  1020
CGCAGTACCA GAAGGAGCTG AATAAGTATT CTACGCACCT GCATCTAGCA GATGATTGTA  1080
TGAAGCACTT CAAGGGCTCG GTGGAGAAGC TGTGTAGTGT GGAGCAGGAC CTGGCCATGG  1140
GCTCCGACGC AGAGGGGGAG AAGATCAAGG ACTCCATGAA GCTGATCGTT CCGGTGCTGC  1200
TGGACGCGGC GGTGCCCGCC TACGACAAGA TCCGGGTCCT GCTGCTCTAC ATCCTCCTTC  1260
GGAATGGTGT GAGTGAGGAG AACCTGGCCA AGCTGATCCA GCATGCCAAT GTACAGGCGC  1320
ACAGCAGCCT CATCCGTAAC CTGGAGCAGC TGGGAGGCAC TGTCACCAAC CCCGGGGGCT  1380
CGGGGACCTC CAGCCGGCTG GAGCCGAGAG AACGCATGGA GCCCACCTAT CAGCTGTCCC  1440
GCTGGACCCC GGTCATCAAG GATGTAATGG AGGACGCCGT GGAGGACCGG CTGGACAGGA  1500
ACCTGTGGCC CTTCGTATCC GACCCCGCCC CCACGGCCAG CTCCCAGGCC GCTGTCAGTG  1560
CCCGCTTCGG TCACTGGCAC AAGAACAAGG CTGGCGTAGA AGCCCGGGCG GGCCCCCGGC  1620
TCATCGTGTA TGTCATGGGC GGTGTGGCCA TGTCAGAGAT GAGGGCCGCC TACGAGGTGA  1680
CCAGGGCCAC CGAGGGCAAG TGGGAGGTGC TCATTGGCTC CTCACACATC CTCACCCCGA  1740
CCCGCTTCCT GGATGACCTG AAGGCACTGG ACAAGAAGCT GGAGGACATT GCCCTGCCCT  1800
GACCCCTGGC CCCGCCCCCT ACCCCTCCCT TTCCAGAGAA ATAAACTCTT CCCGTCGCTC  1860
```

-continued

```
TGCCAAGATT ATCATGTCTC AGCCTCCTGC TACCCATTAC AGGTGAGAAA TGTATCTCTT    1920

AATCTACGAG ATCTCATTGG CCTTACGTTT CAGCCATACG TTTATTACCT GTATGATGCC    1980

CTTTCCTATA TCGTGCCTCT ACCTGTTCGG ATCCTATTCT ATGGCCTCCT GGGAAGGTTT    2040

ACGATGGTCA CCCCAGTCTT GCTTCTCGCT ATTACAAAAG CTATGTCTG GCTATTCTAC     2100

CACGGAGACT CTGCCGTTCC TTGTTTAAGC GGTTACCTAT AATGCTGAGC CTCTTAGAAC    2160

CAGTACAAAA GTTCCTAGCA ATTGCATGTG AAGGATTCC CGGAGGTCAA TCTTGCCTTT     2220

ACCCCAATTC TTAAGCTTGG AACCTTTTCA CCTGTTTGGC TAATTCTCCC GGCGGGTTTC    2280

CCCCACGCTG TAAAGGT                                                   2297
```

(2) INFORMATION FOR SEQ ID NO:3:

(i) SEQUENCE CHARACTERISTICS:
        (A) LENGTH: 593 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 642026

(xi) SEQUENCE DESCRIPTION: SEQ ID NO:3:

```
Met Ala Pro Leu Gly Leu Lys Ala Val Val Gly Glu Lys Ile Leu Ser
 1               5                  10                  15

Gly Val Ile Arg Ser Val Lys Lys Asp Gly Glu Trp Lys Val Leu Ile
             20                  25                  30

Met Asp His Pro Ser Met Arg Ile Leu Ser Ser Cys Cys Lys Met Ser
         35                  40                  45

Asp Ile Leu Ala Glu Gly Ile Thr Ile Val Glu Asp Ile Asn Lys Arg
     50                  55                  60

Arg Glu Pro Ile Pro Ser Leu Glu Ala Ile Tyr Leu Leu Ser Pro Thr
 65                  70                  75                  80

Glu Lys Ser Val Gln Ala Leu Ile Ala Asp Phe Gln Gly Thr Pro Thr
                 85                  90                  95

Phe Thr Tyr Lys Ala Ala His Ile Phe Phe Thr Asp Thr Cys Pro Glu
             100                 105                 110

Pro Leu Phe Ser Glu Leu Gly Arg Ser Arg Leu Ala Lys Ala Val Lys
         115                 120                 125

Thr Leu Lys Glu Ile His Leu Ala Phe Leu Pro Tyr Glu Ala Gln Val
     130                 135                 140

Phe Ser Leu Asp Ala Pro His Ser Thr Tyr Asn Leu Tyr Cys Pro Phe
145                 150                 155                 160

Arg Ala Gly Glu Arg Gly Arg Gln Leu Asp Ala Leu Ala Gln Gln Ile
                 165                 170                 175

Ala Thr Leu Cys Ala Thr Leu Gln Glu Tyr Pro Ser Ile Arg Tyr Arg
             180                 185                 190

Lys Gly Pro Glu Asp Thr Ala Gln Leu Ala His Ala Val Leu Ala Lys
         195                 200                 205

Leu Asn Ala Phe Lys Ala Asp Thr Pro Ser Leu Gly Glu Gly Pro Glu
     210                 215                 220

Lys Thr Arg Ser Gln Leu Leu Ile Met Asp Arg Ala Ala Asp Pro Val
225                 230                 235                 240

Ser Pro Leu Leu His Glu Leu Thr Phe Gln Ala Met Ala Tyr Asp Leu
                 245                 250                 255

Leu Asp Ile Glu Gln Asp Thr Tyr Arg Tyr Glu Thr Thr Gly Leu Ser
```

```
                260               265               270
Glu Ser Arg Glu Lys Ala Val Leu Asp Glu Asp Asp Leu Trp
            275               280               285
Val Glu Leu Arg His Met His Ile Ala Asp Val Ser Lys Lys Val Thr
290                 295               300
Glu Leu Lys Thr Phe Cys Glu Ser Lys Arg Leu Thr Thr Asp Lys
305               310               315               320
Ala Asn Ile Lys Asp Leu Ser His Ile Leu Lys Met Pro Gln Tyr
                325               330               335
Gln Lys Glu Leu Asn Lys Tyr Ser Thr His Leu His Leu Ala Asp Asp
                340               345               350
Cys Met Lys His Phe Lys Gly Ser Val Glu Lys Leu Cys Ser Val Glu
                355               360               365
Gln Asp Leu Ala Met Gly Ser Asp Ala Glu Gly Lys Ile Lys Asp
370                 375               380
Ala Met Lys Leu Ile Val Pro Val Leu Leu Asp Ala Ser Val Pro Pro
385                 390               395               400
Tyr Asp Lys Ile Arg Val Leu Leu Tyr Ile Leu Leu Arg Asn Gly
                405               410               415
Val Ser Glu Glu Asn Leu Ala Lys Leu Ile Gln His Ala Asn Val Gln
                420               425               430
Ser Tyr Ser Ser Leu Ile Arg Asn Leu Glu Gln Leu Gly Gly Thr Val
                435               440               445
Thr Asn Ser Ala Gly Ser Gly Thr Ser Ser Arg Leu Glu Arg Arg Glu
450                 455               460
Arg Met Glu Pro Thr Tyr Gln Leu Ser Arg Trp Ser Pro Val Ile Lys
465                 470               475               480
Asp Val Met Glu Asp Val Val Glu Asp Arg Leu Asp Arg Lys Leu Trp
                485               490               495
Pro Phe Val Ser Asp Pro Ala Pro Val Pro Ser Ser Gln Ala Ala Val
                500               505               510
Ser Ala Arg Phe Gly His Trp His Lys Asn Lys Ala Gly Val Glu Ala
                515               520               525
Arg Ala Gly Pro Arg Leu Ile Val Tyr Ile Val Gly Gly Val Ala Met
530                 535               540
Ser Glu Met Arg Ala Ala Tyr Glu Val Thr Arg Ala Thr Glu Gly Lys
545                 550               555               560
Trp Glu Val Leu Ile Gly Ser Ser His Ile Leu Thr Pro Thr Arg Phe
                565               570               575
Leu Asp Asp Leu Lys Thr Leu Asp Gln Lys Leu Glu Gly Val Ala Leu
                580               585               590
Pro (2) INFORMATION FOR SEQ ID NO:4:

(i) SEQUENCE CHARACTERISTICS:
         (A) LENGTH: 593 amino acids
         (B) TYPE: amino acid
         (C) STRANDEDNESS: single
         (D) TOPOLOGY: linear (vii) IMMEDIATE SOURCE:
         (A) LIBRARY: GenBank
         (B) CLONE: 1246217

(xi) SEQUENCE DESCRIPTION: SEQ ID NO:4:

Met Ala Pro Ser Gly Leu Lys Glu Val Val Gly Glu Lys Ile Leu Asn
```

```
            1               5                    10                   15
        Gly Val Ile Arg Ser Val Lys Lys Asp Gly Glu Trp Lys Val Leu Ile
                        20                  25                  30

Met Asp His Pro Ser Met Arg Ile Leu Ser Ser Cys Cys Lys Met Ser
                        35                  40                  45

Asp Ile Leu Ala Glu Gly Ile Thr Ile Val Glu Asp Ile Asn Lys Arg
                        50                  55                  60

Arg Glu Pro Ile Pro Ser Leu Glu Ala Ile Tyr Leu Leu Ser Pro Thr
         65                 70                  75                  80

Glu Lys Ser Val Gln Ala Leu Ile Ala Asp Phe Arg Gly Thr Pro Thr
                        85                  90                  95

Phe Thr Tyr Lys Ala Ala His Ile Phe Phe Thr Asp Thr Cys Pro Glu
                        100                 105                 110

Pro Leu Phe Thr Glu Leu Ser Arg Ser Arg Leu Ala Lys Val Val Lys
                        115                 120                 125

Thr Leu Lys Glu Ile His Leu Ala Phe Leu Pro Tyr Glu Ala Gln Val
                        130                 135                 140

Phe Ser Leu Asp Ala Pro His Ser Thr Tyr Asn Leu Tyr Cys Pro Phe
        145                 150                 155                 160

Arg Val Gly Glu Arg Ala Arg Gln Ile Glu Ala Leu Ala Gln Gln Ile
                        165                 170                 175

Ala Thr Leu Cys Ala Thr Leu Gln Glu Tyr Pro Ala Ile Arg Tyr Arg
                        180                 185                 190

Lys Gly Pro Glu Val Thr Ala Gln Leu Ala Asn Ala Val Leu Ala Lys
                        195                 200                 205

Leu Asn Ala Phe Lys Ala Asp Asn Pro Ser Leu Gly Glu Gly Pro Glu
                        210                 215                 220

Lys Thr Arg Ser Gln Leu Leu Ile Val Asp Arg Gly Ala Asp Pro Val
        225                 230                 235                 240

Ser Pro Leu Leu His Glu Leu Thr Phe Gln Ala Met Ala Tyr Asp Leu
                        245                 250                 255

Leu Asn Ile Glu Gln Asp Thr Tyr Arg Tyr Glu Thr Thr Gly Leu Ser
                        260                 265                 270

Glu Ala Arg Glu Lys Ala Val Leu Leu Asp Glu Asp Asp Asp Leu Trp
                        275                 280                 285

Val Glu Leu Arg His Met His Ile Ala Asp Val Ser Lys Lys Val Thr
                        290                 295                 300

Glu Leu Leu Lys Thr Phe Cys Glu Ser Lys Arg Leu Thr Thr Asp Lys
        305                 310                 315                 320

Ala Asn Ile Lys Asp Leu Ser His Ile Leu Lys Lys Met Pro Gln Tyr
                        325                 330                 335

Gln Lys Glu Leu Asn Lys Tyr Ser Thr His Leu His Leu Ala Asp Asp
                        340                 345                 350

Cys Met Lys His Phe Lys Gly Ser Val Glu Lys Leu Cys Gly Val Glu
                        355                 360                 365

Gln Asp Leu Ala Met Gly Ser Asp Thr Glu Gly Glu Lys Ile Lys Asp
                        370                 375                 380

Ala Met Lys Leu Ile Val Pro Val Leu Leu Asp Ala Ala Val Pro Ala
        385                 390                 395                 400

Tyr Asp Lys Ile Arg Val Leu Leu Tyr Ile Leu Leu Arg Asn Gly
                        405                 410                 415

Val Ser Glu Glu Asn Leu Ala Lys Leu Ile Gln His Ala Asn Val Gln
                        420                 425                 430
```

-continued

```
Ala His Ser Ser Leu Ile Arg Asn Leu Glu Gln Leu Gly Gly Thr Val
        435                 440                 445

Thr Asn Pro Gly Gly Pro Gly Thr Ser Ser Arg Leu Glu Arg Arg Glu
    450                 455                 460

Arg Leu Glu Pro Thr Tyr Gln Leu Ser Arg Trp Thr Pro Val Ile Lys
465                 470                 475                 480

Asp Val Met Glu Asp Ala Val Glu Asp Arg Leu Asp Arg Lys Leu Trp
                485                 490                 495

Pro Phe Val Ser Asp Pro Ala Pro Thr Ser Ser Ser Gln Ala Ala Val
                500                 505                 510

Ser Ala Arg Phe Gly His Trp His Lys Asn Lys Ala Gly Val Glu Met
        515                 520                 525

Arg Ala Gly Pro Arg Leu Ile Ile Tyr Val Met Gly Gly Val Ala Met
        530                 535                 540

Ser Glu Met Arg Ala Ala Tyr Glu Val Thr Arg Ala Thr Asp Gly Lys
545                 550                 555                 560

Trp Glu Val Leu Ile Gly Ser Ser His Ile Leu Thr Pro Thr Arg Phe
                565                 570                 575

Leu Asp Asp Leu Lys Thr Leu Asp Gln Lys Leu Glu Asp Ile Ala Leu
                580                 585                 590

Pro
```